(12) United States Patent
Salciccioli et al.

(10) Patent No.: US 10,647,640 B2
(45) Date of Patent: May 12, 2020

(54) PROCESS FOR CONVERTING ALKANES TO PARA-XYLENE

(71) Applicant: ExxonMobil Chemical Patents Inc., Baytown, TX (US)

(72) Inventors: Michael Salciccioli, Houston, TX (US); Hari Nair, Somerville, NJ (US); Glenn C. Wood, Houston, TX (US); Nikolaos Soultanidis, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/775,466

(22) PCT Filed: Dec. 5, 2016

(86) PCT No.: PCT/US2016/064928
§ 371 (c)(1),
(2) Date: May 11, 2018

(87) PCT Pub. No.: WO2017/131862
PCT Pub. Date: Aug. 3, 2017

(65) Prior Publication Data
US 2018/0370874 A1     Dec. 27, 2018

Related U.S. Application Data

(60) Provisional application No. 62/288,902, filed on Jan. 29, 2016.

(30) Foreign Application Priority Data

Mar. 15, 2016   (EP) .................................. 16160374

(51) Int. Cl.
*C07C 6/12*     (2006.01)
*C07C 1/20*     (2006.01)
*C07C 5/27*     (2006.01)

(52) U.S. Cl.
CPC ................ *C07C 6/126* (2013.01); *C07C 1/20* (2013.01); *C07C 5/277* (2013.01); *C07C 5/2732* (2013.01);
(Continued)

(58) Field of Classification Search
CPC ........... C07C 6/126; C07C 1/20; C07C 5/227; C07C 5/2732; C07C 2529/40; Y02P 20/52
See application file for complete search history.

(56) References Cited

U.S. PATENT DOCUMENTS 3,894,102 A   7/1975  Chang et al.
3,894,103 A   7/1975  Chang et al.
(Continued)

OTHER PUBLICATIONS

Tao, L., et al., "Catalytic Conversion of CH3Br to Aromatics Over PbO-Modified HZSM-5", Applied Catalysis A: General, vol. 367, Issues 1-2, pp. 99-107, 2009.
(Continued)

*Primary Examiner* — Ali Z Fadhel

(57) ABSTRACT

Systems and methods are provided for forming para-xylene from aromatics-containing streams having reduced or minimized amounts of $C_{2+}$ side chains. Reduced or minimized amounts of $C_{2+}$ side chains can provide benefits for improving and/or allowing modification of transalkylation conditions, xylene isomerization conditions, or a combination thereof. Such aromatics-containing streams can be formed, for example, by conversion of methyl halide, methanol, syngas, and/or dimethyl ether to aromatics by an aromatic conversion process. The methyl halide, methanol, syngas, and/or dimethyl ether can be formed by conversion of methane.

14 Claims, 4 Drawing Sheets

(52) U.S. Cl.
CPC ........ *C07C 5/2737* (2013.01); *C07C 2529/40* (2013.01); *Y02P 20/52* (2015.11)

(56) References Cited

U.S. PATENT DOCUMENTS

| | | | |
|---|---|---|---|
| 3,894,104 | A | 7/1975 | Chang et al. |
| 3,894,107 | A | 7/1975 | Butter et al. |
| 4,035,430 | A | 7/1977 | Dwyer et al. |
| 4,049,573 | A | 9/1977 | Kaeding |
| 4,058,576 | A | 11/1977 | Chang et al. |
| 4,088,706 | A | 5/1978 | Kaeding |
| 5,043,502 | A | 8/1991 | Martindale et al. |
| 5,936,135 | A | 8/1999 | Choudhary et al. |
| 6,855,854 | B1* | 2/2005 | James, Jr. ............... C07C 6/126 585/319 |
| 7,579,510 | B2 | 8/2009 | Gadewar et al. |
| 7,998,438 | B2 | 8/2011 | Weiss |
| 8,017,822 | B2 | 9/2011 | Fong et al. |
| 8,697,929 | B2 | 4/2014 | Ou et al. |
| 2004/0186330 | A1 | 9/2004 | Kong et al. |
| 2005/0266979 | A1* | 12/2005 | Boldingh ............... B01J 23/36 502/64 |
| 2006/0149105 | A1* | 7/2006 | Krawczyk ............... C07C 6/126 585/475 |
| 2007/0299289 | A1* | 12/2007 | Bresler ................. C07C 5/2708 585/323 |
| 2010/0099930 | A1 | 4/2010 | Stoimenov et al. |
| 2010/0152508 | A1 | 6/2010 | Ou et al. |
| 2013/0158324 | A1 | 6/2013 | Waycuilis et al. |
| 2013/0267746 | A1* | 10/2013 | Ding ........................ C07C 6/06 585/319 |
| 2015/0175499 | A1* | 6/2015 | Ou ........................... C07C 1/22 585/408 |
| 2015/0299071 | A1* | 10/2015 | Ou ......................... C07C 5/2729 585/300 |

OTHER PUBLICATIONS

Ouyang, Q. et al., "A New Catalytic Process for High-Efficiency Synthesis of p-xylene by Methylation of Toulene with CH3Br", AlChE Journal, vol. 59, Issue 2, pp. 532-540, 2013. DOI10.1002/aic.13822.

\* cited by examiner

PROCESS FOR CONVERTING ALKANES TO PARA-XYLENE

CROSS-REFERENCE OF RELATED APPLICATIONS

This application is a National Phase Application claiming priority to PCT Application Serial No. PCT/US2016/064928, filed Dec. 5, 2016, which claims priority to and the benefit of U.S. Provisional Application No. 62/288,902, filed on Jan. 29, 2016 and EP Application No. 16160374.1, filed Mar. 15, 2016, the disclosures of which are incorporated herein by reference in their entireties.

FIELD OF THE INVENTION

Systems and methods are provided for converting alkanes, alkyl halides, and/or alcohols to aromatics.

BACKGROUND OF THE INVENTION

Conversion of aliphatic compounds to aromatics is an ongoing area of study for chemical manufacture. Certain aromatic compounds, such as para-xylene, have a relatively high commercial value. Processes that can allow formation of aromatics from feed streams that primarily have fuel value, such as natural gas or fuel gas, can be beneficial if the conversion to aromatics can be performed at a reasonable cost. Due to the relatively low activity of alkanes in processes for direct conversion to aromatics, additional improvements in processes for conversion of alkanes to aromatics are desirable.

U.S. Pat. No. 5,043,502 describes a method for dehydroaromatization of $C_2$-$C_5$ aliphatic hydrocarbons to form aromatics. Para-xylene is produced both from the dehydroaromatization reaction and from subsequent methylation of toluene generated by the dehydroaromatization reaction. Benzene is also produced from dehydroaromatization and is described as being methylated to toluene during the subsequent methylation.

Other conventional processes can utilize feeds containing methane. Although methane is abundant, its relative inertness has limited its utility in these conversion processes. For example, oxidative coupling methods generally involve highly exothermic methane combustion reactions, frequently require expensive oxygen generation facilities, and produce large quantities of low value carbon oxides. Non-oxidative methane aromatization is equilibrium-limited, and temperatures ≥about 800° C. are needed for methane conversions greater than a few percent.

To obviate these problems, catalytic processes have been proposed for co-converting methane and one or more co-reactants to higher hydrocarbon, such as aromatics. For example, U.S. Pat. No. 5,936,135 discloses reacting methane at a temperature in the range of 300° C. to 600° C. with (i) a $C_{2-10}$ olefin and/or (ii) a $C_{2-10}$ paraffin in the presence of a bi-functional pentasil zeolite catalyst, having strong dehydrogenation and acid sites, to produce aromatics. The preferred mole ratio of olefin and/or higher paraffin to methane and/or ethane in the feed ranges from about 0.2 to about 2.0.

U.S. Pat. Nos. 4,049,573 and 4,088,706 disclose conversion of methanol to a hydrocarbon mixture rich in $C_2$-$C_3$ olefins and mononuclear aromatics, particularly para-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

Methanol can be converted to gasoline employing the MTG (methanol-to-gasoline) process. The MTG process is disclosed in the patent art, including, for example, U.S. Pat. Nos. 3,894,103; 3,894,104; 3,894,107; 4,035,430; and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}$+ olefin precursors of the desired distillate are rapidly converted via hydrogen transfer to heavy polymethylaromatics and $C_4$ to $C_8$ isoparaffins under methanol conversion conditions.

U.S. Publication 2013/0158324 describes a method for conversion of alkanes to heavier hydrocarbons via an alkyl halide intermediate. The types of hydrocarbons produced by the conversion reaction, including aromatics, can vary depending on the reaction conditions.

It is desirable to improve the conversion of alkanes to aromatics and ultimately increase the yield of para-xylene.

SUMMARY OF THE INVENTION

The present invention is directed to systems and methods for forming para-xylene from aromatics-containing streams having reduced or minimized amounts of $C_{2+}$ side chains. Reduced or minimized amounts of $C_{2+}$ side chains can provide benefits for improving and/or allowing modification of transalkylation conditions, xylene isomerization conditions, or a combination thereof. Such aromatics-containing streams can be formed, for example, by conversion of methyl halide, methanol, syngas, and/or dimethyl ether to aromatics by an aromatic conversion process, which can be formed by conversion of methane.

In one aspect, a first $C_8$ aromatics stream and a $C_{9+}$ aromatics stream is separated from an aromatic hydrocarbon feed stream that has 5 wt % or less of aromatics with $C_{2+}$ side chains based on the total aromatics content of the aromatic hydrocarbon feed stream. The $C_{9+}$ aromatics stream is exposed to effective transalkylation conditions to form a transalkylation effluent having a greater weight percent of $C_8$ aromatics than the $C_{9+}$ aromatics stream. The effective transalkylation conditions can include i) liquid phase transalkylation conditions; ii) a transalkylation catalyst comprising 0.1 wt % or less of a Group VIII metal; iii) a transalkylation catalyst having an alpha value of 10 or less; or iv) a combination of two or more of i), ii), and iii). A second $C_8$ aromatics stream is separated from the transalkylation effluent. A para-xylene enriched fraction is then separated from the first $C_8$ aromatics stream and the second $C_8$ aromatics stream, the para-xylene enriched fraction having a greater weight percent of para-xylene than the weight percent of para-xylene in the first $C_8$ aromatics stream and the second $C_8$ aromatics stream. Optionally, separating a para-xylene enriched fraction from the first $C_8$ aromatics stream and the second $C_8$ aromatics stream can further include separating a para-xylene depleted fraction from the first $C_8$ aromatics stream and the second $C_8$ aromatics stream. Optionally, the para-xylene depleted fraction can be isomerized to form an isomerized product stream having a greater weight percent of para-xylene than the weight percent of para-xylene in the para-xylene depleted fraction.

In another aspect, a first $C_8$ aromatics stream and a $C_{9+}$ aromatics stream is separated from an aromatic hydrocarbon feed stream having an ethylbenzene content of 5 wt % or less based on the total aromatics content of the aromatic hydrocarbon feed stream. A first para-xylene enriched fraction and a first para-xylene depleted fraction is separated from the first $C_8$ aromatics stream, the para-xylene enriched fraction having a greater weight percent of para-xylene than the weight percent of para-xylene in the first $C_8$ aromatics stream. The para-xylene depleted fraction is isomerized to form an isomerized product having a greater weight percent of para-xylene than the weight percent of para-xylene in the para-xylene depleted fraction and a para-methyl-ethylbenzene content of about 0.1 wt % or less. A second para-xylene enriched fraction and a second para-xylene depleted fraction is separated from the isomerized stream, the second para-xylene enriched fraction having a greater weight percent of para-xylene than the weight percent of para-xylene in the isomerized product stream.

In still another aspect, a first $C_8$ aromatics stream and a $C_{9+}$ aromatics stream is separated from an aromatic hydrocarbon feed stream having an ethylbenzene content of 5 wt % or less based on the total aromatics content of the aromatic hydrocarbon feed stream. A first para-xylene enriched fraction and a first para-xylene depleted fraction is separated from the first $C_8$ aromatics stream using a simulated moving bed separator. The first para-xylene enriched fraction has a greater weight percent of para-xylene than the weight percent of para-xylene in the first $C_8$ aromatics stream. A separation purge stream is separated from the para-xylene depleted fraction, the weight ratio of the separation purge stream to the first para-xylene enriched fraction being 0.2 or less. The first para-xylene depleted fraction is then isomerized under effective liquid phase isomerization conditions to form an isomerized product stream having a greater weight percent of para-xylene than the para-xylene depleted fraction.

DETAILED DESCRIPTION OF THE EMBODIMENTS

Overview and Definitions

Figure 1:
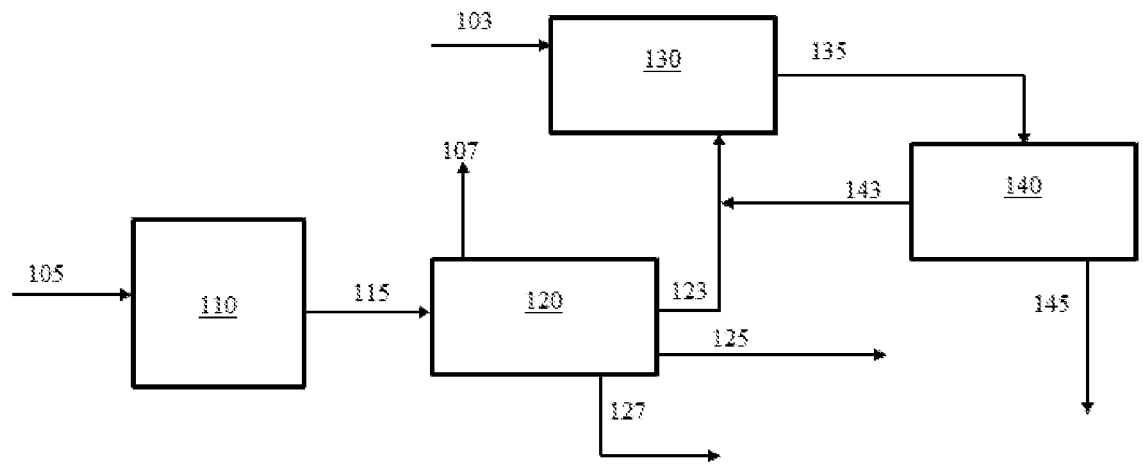
FIG. 1 schematically shows an example of a reaction system for converting a feed to form aromatics.

In various aspects, systems and methods are provided for converting alkanes while generating improved yields of desirable aromatics and/or improved selectivity for forming desired aromatics, e.g., xylenes such as para-xylene (para-xylene). It has been discovered that using methyl halides, methanol and/or dimethyl ether, or more generally alkyl halides and/or alcohols, as a feed for forming aromatic hydrocarbons can allow for preferential formation of aromatics with methyl side chains. The number of methyl side chains can vary depending on the aromatic formation conditions. This is in contrast to various other conventional aromatics formation processes which can tend to produce larger percentages of aromatics that are substituted with larger alkyl chains.

By preferentially forming aromatics with methyl side chains, a variety of advantages can be achieved during subsequent processing to form and/or isolate para-xylene. In some aspects, an aromatics stream having a reduced or minimized content of ethyl (or larger) alkyl substituents can be readily converted to para-xylene. This can correspond to methylation of $C_6$ and/or $C_7$ aromatics as well as transalkylation of $C_9$ aromatics. Having a reduced content of $C_{9+}$ aromatics with ethyl or larger side chains (for example, methylethylbenzene and/or cumene and/or diethylbenzene) can also provide additional advantages for transalkylation with regard to the transalkylation conditions and/or catalyst. One of the limitations on conventional transalkylation is the requirement to perform some dealkylation during the transalkylation, so that aromatics with $C_{2+}$ alkyl side chains (such as methylethylbenzene) can be converted to other types of aromatics. A feed with a sufficiently low content of $C_{9+}$ aromatics that include $C_{2+}$ side chains can relax this requirement, allowing other types of catalysts to be used and/or potentially allowing liquid phase conditions to be used.

In other additional or alternate aspects, an aromatics stream having a reduced or minimized amount of ethyl (or larger) substituents can be advantageous for improving the yield of para-xylene from a xylene isomerization loop. Ethylbenzene is a $C_8$ aromatic that can present difficulties during para-xylene separation and xylene isomerization. For example, during xylene isomerization ethylbenzene can be converted via a side reaction into para-methyl-ethylbenzene, which is difficult to separate from $C_8$ aromatics via distillation. Reducing or minimizing the ethylbenzene content in a $C_8$ aromatics feed can improve conventional $C_8$ isomerization methods and/or enable improved isomerization methods.

Production of a desired aromatic stream from an alkane-containing feed can correspond to a series of processes. Each process can include one or more stages, such as reaction stages or separation stages. For example, an initial process can correspond to an aromatic formation process, where compounds containing aromatic rings are formed from alkanes. A first separation process can separate one or more streams containing aromatic compounds from the aromatic formation effluent. At least one of the streams containing aromatic compounds can be passed into a methylation process. A second separation process can separate one or more streams containing aromatic compounds from the aromatic effluent. For aspects where a desired product is a xylene, streams from the aromatic formation process and the methylation process can be separated in a third separation process to separate a desired xylene from other $C_8$ compounds.

An example of a system suitable for converting alkanes to para-xylene is shown in FIG. 1. A feed 105 containing one or more $C_1$-$C_9$ alkanes is introduced into aromatic formation process 110 for conversion of alkanes to aromatics. The aromatic formation process 110 can represent a series of process steps. The series of process steps can optionally start with conversion of methane (or other alkanes) to methyl halides (or other alkyl halides), syngas and/or methanol (or other alcohols), or a combination thereof. The methyl halides and/or methanol can then be converted into aromatics with a reduced or minimized content of aromatic compounds with $C_{2+}$ side chains. The effluent 115 from aromatic formation process 110 can then be separated in an initial separation process 120. The initial separation process can be used to separate from the effluent 115 at least a fraction 125, which contains at least a portion of the effluent's $C_8$ aromatics, and a fraction 123, which contains at least a portion of the effluent's $C_6$ and $C_7$ aromatics. Optionally, a $C_9+$ stream 127 can also be separated from the effluent 115. A lower boiling (including unconverted) fraction 107 corresponding to primarily $C_{6-}$ and/or non-aromatic compounds can also be separated, and optionally recycled (not shown) to the aromatic formation process 110. The fraction 123 is introduced into a methylation process 130 along with a methylating agent feed 103 to produce $C_8$ aromatics from $C_6$ and $C_7$ aromatics in fraction 123. The methylation effluent 135 from the methylation process 130 is conducted to a second separator 140 to separate from the methylation effluent 135 at least a fraction 145, which contains at least a portion of the methylation effluent's $C_8$ aromatics and a fraction 143, which contains at least a portion of the methylation effluent's $C_6$ and $C_7$ aromatics. Optionally, initial separation process 120 and second separation process 140 can be combined into a single separator and/or process, such as by using a divided wall column separator. An example of a divided wall column separator is described in U.S. Publication 2011/0132803, which is incorporated herein by reference with respect to its description of a divided wall column separator. Optionally, initial separation process 120 and second separation process 140 can be combined into a single separator without maintaining the separate identity of product $C_8$ streams.

Figure 2:
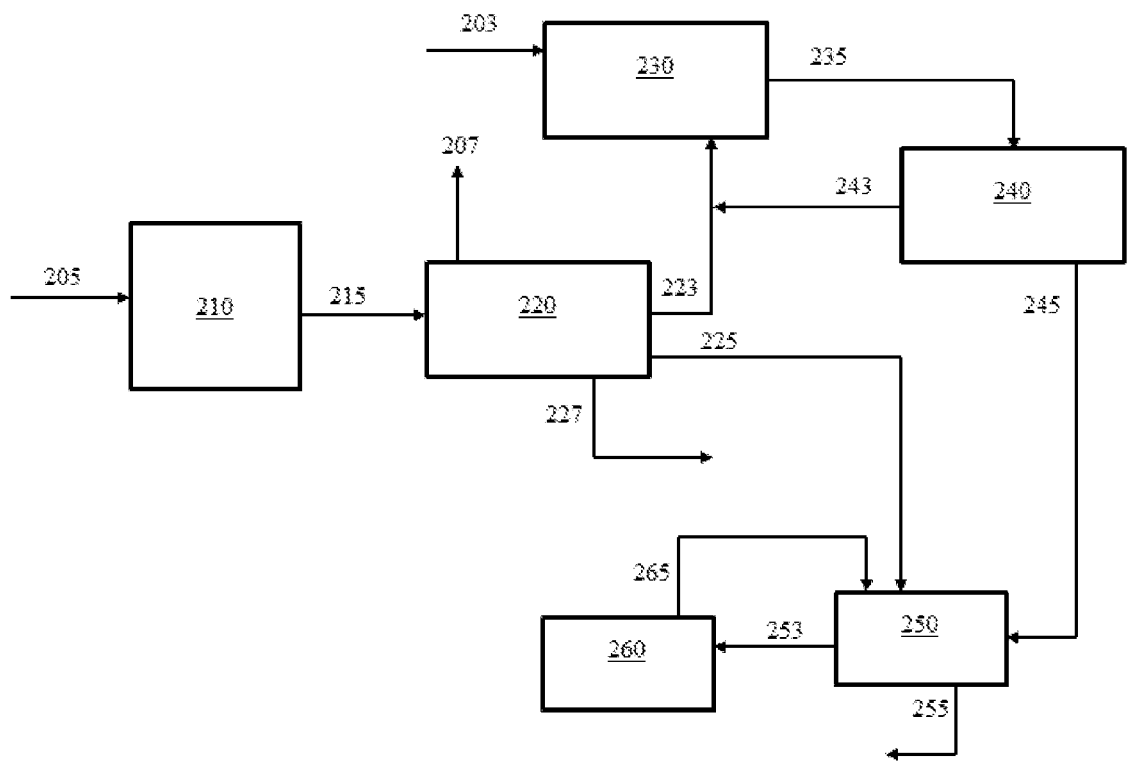
FIG. 2 schematically shows another example of a reaction system for converting a feed to form aromatics.

FIG. 2 shows an example of a system that includes a xylene separation and isomerization loop for producing a para-xylene enriched product. It is noted that similar index numbers between figures correspond to similar components. An alkane-containing feed 205 is introduced into an aromatic formation process 210. The effluent 215 from aromatic formation process 210 is then passed into a first separation process 220, which separates at least fractions 223 and 225 from effluent 215. Fraction 225 contains at least a portion of the $C_8$ aromatics from effluent 215 and fraction 223 contains at least a portion of the $C_6$ and $C_7$ aromatics from effluent 215. A lower boiling (including unconverted) fraction 207 can also be separated from effluent 215 and, optionally, returned (at least in part) to the aromatic formation process 210. Optionally, a stream 227 is separated from effluent 215 in first separation process 220. Stream 227 can comprise, e.g., at least a portion of any $C_9+$ hydrocarbons in effluent 215. In certain aspects, stream 227 comprises what remains of the effluent after the separation of fractions 223, 225, and/or 207. Fraction 223 is introduced into a methylation process 230 along with a methylating agent feed 203 (e.g., methanol) to produce $C_8$ aromatics by methylating at least a portion of the $C_6$ and/or $C_7$ aromatics in fraction 223. The effluent 235 from the methylation process 230 is conducted to a second separation process 240 to separate at least fractions 243 and 245 from methylation effluent 235. Fraction 245 contains at least a portion of the $C_8$ aromatics from effluent 235, and fraction 243 contains at least a portion of the $C_6$ and $C_7$ aromatics from effluent 235. Fractions 225 and 245 are passed to the third separation process 250 for separation of para-xylene from other $C_8$ aromatics. In third separation process 250, a stream 255 enriched in para-xylene and a stream 253 depleted in para-xylene are separated from fractions 225 and 245. The stream 253 depleted in para-xylene is passed into isomerization process 260 for conversion of ortho- and meta-xylene into para-xylene. The resulting effluent stream 265, with an increased amount of para-xylene relative to stream 253, is returned to the third separation process 250 for separation of the para-xylene. Optionally, stream 265 can be introduced into the third separation process 250 at a different separation stage than the input separation stage for stream 225, which can allow the third separation process 250 to take advantage of differing concentrations of para-xylene in stream 265 and 225. For example, a stream having a higher para-xylene concentration can be introduced into separation process 250 at a later separation stage. This can allow earlier separation stages to have a smaller processing capacity. Since the earlier separation stages in a separator correspond to stages with the largest volume (i.e., due to lower concentration of the separation target), reducing the input flows to early separation stages can reduce the required size for the potentially largest stages within a multi-stage separator. Optionally, stream 245 can be introduced into the third separation process 250 at a different stage than the input stage(s) for stream 225 and stream 265, which can allow the third separation process 250 to take advantage of differing concentrations of para-xylene in streams 225, 245, and/or 265. Alternatively, at least a portion of effluent 235 can be conducted to separation process 220, for separating streams 243 and/or 245. In other words, at least part of the separation functionality of separation process 240 can be carried out in separation process 220. Optionally, first separation process 220 and second separation process 240 can be combined into a single separator and/or process, such as by using a divided wall column separator.

Figure 3:
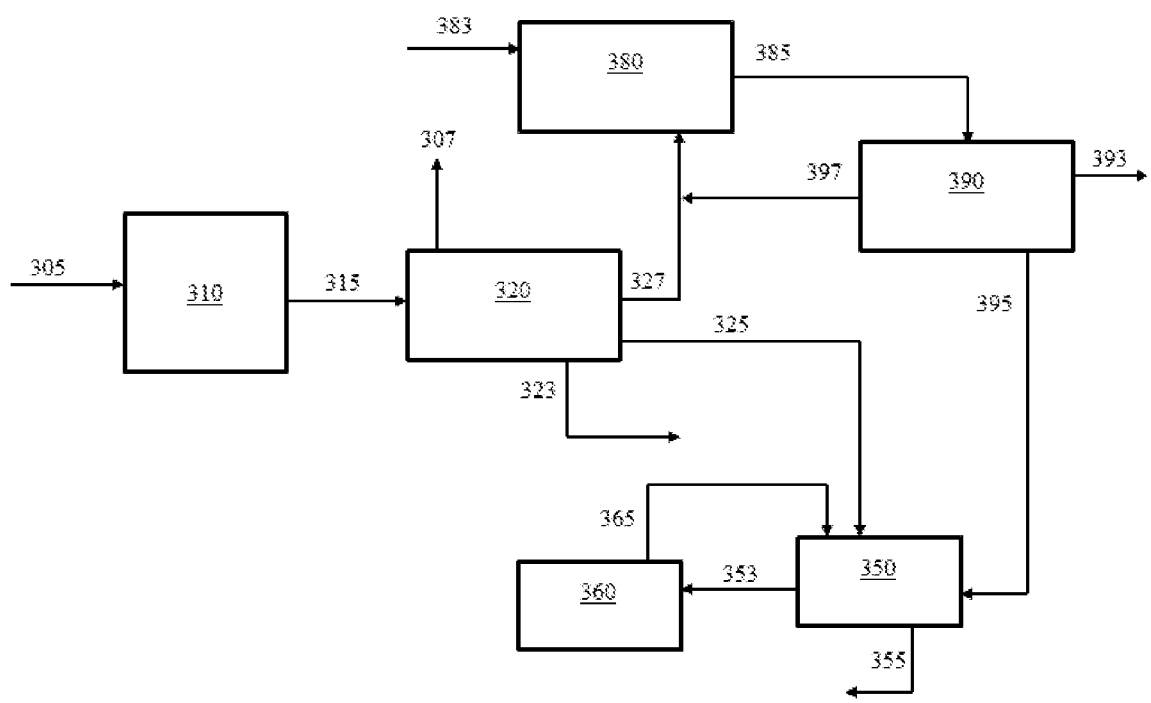
FIG. 3 schematically shows another example of a reaction system for converting a feed to form aromatics.

The configuration in FIG. 2 explicitly showed the integration of methylation of $C_6$ and $C_7$ aromatics as part of a process for para-xylene production. FIG. 3 shows an example of integration of transalkylation of $C_9$ or $C_{9+}$ aromatics as part of para-xylene production. Although FIGS. 2 and 3 separately show integration of methylation and transalkylation, this is only for convenience in illustrating the configurations. It is understood that both methylation and transalkylation can be integrated with para-xylene product. It is further understood that neither is required to be integrated as shown in FIGS. 2 and 3.

It is noted that similar index numbers between figures correspond to similar components. An alkane-containing feed 305 is introduced into an aromatic formation process 310. The effluent 315 from aromatic formation process 310 is then passed into a first separation process 320, which separates at least fractions 323 and 325 from effluent 315. Fraction 325 contains at least a portion of the $C_8$ aromatics from effluent 315 and fraction 323 contains at least a portion of the $C_6$ and $C_7$ aromatics from effluent 315. A lower boiling (including unconverted) fraction 307 can also be separated from effluent 315 and, optionally, returned (at least in part) to the aromatic formation process 310. A stream 327 corresponding to $C_9$ (or optionally $C_{9+}$) aromatics is also separated from effluent 315 in first separation process 320. Stream 327 is introduced into a transalkylation process 380 along with a $C_6$ and/or $C_7$ feed 383 to produce $C_8$ aromatics by transalkylation. It is noted that $C_6$ and/or $C_7$ feed 383 can include at least a portion of the $C_6$ and $C_7$ aromatics from fraction 323. The effluent 385 from the transalkylation process 380 is conducted to a second separation process 390 to separate at least fractions 393, 395, and 397 from transalkylation effluent 385. Fraction 395 contains at least a portion of the $C_8$ aromatics from effluent 385, fraction 393 contains at least a portion of the $C_6$ and $C_7$ aromatics from effluent 385, and fraction 397 contains at least a portion of the $C_{9+}$ aromatics from effluent 385. In FIG. 3, fractions 325 and 395 are passed to the third separation process 350 for separation of para-xylene from other $C_8$ aromatics. In third separation process 350, a stream 355 enriched in para-xylene and a stream 353 depleted in para-xylene are separated from fractions 325 and 395. The stream 353 depleted in para-xylene is passed into isomerization process 360 for conversion of ortho- and meta-xylene into para-xylene. The resulting effluent stream 365 with an increased amount of para-xylene relative to stream 353 is returned to the third separation process 350 for separation of the para-xylene. Optionally, stream 365 can be introduced into the third separation process 350 at a different separation stage than the input separation stage for stream 325, which can allow the third separation process 350 to take advantage of differing concentrations of para-xylene in stream 365 and 325. For example, a stream having a higher para-xylene concentration can be introduced into separation process 350 at a later separation stage. This can allow earlier separation stages to have a smaller processing capacity. Since the earlier separation stages in a separator correspond to stages with the largest volume (i.e., due to lower concentration of the separation target), reducing the input flows to early separation stages can reduce the required size for the potentially largest stages within a multi-stage separator. Optionally, stream 395 can be introduced into the third separation process 350 at a different stage than the input stage(s) for stream 325 and stream 365, which can allow the third separation process 350 to take advantage of differing concentrations of para-xylene in streams 325, 395, and/or 365. Alternatively, at least a portion of effluent 385 can be conducted to separation process 320, for separating streams 393 and/or 395. In other words, at least part of the separation functionality of separation process 390 can be carried out in separation process 320. Optionally, first separation process 320 and second separation process 390 can be combined into a single separator and/or process, such as by using a divided wall column separator.

By using an aromatic formation process based on conversion of methyl halides and/or methanol, the aromatic formation process can be operated to have a reduced or minimized ethylbenzene concentration. One option for characterizing the ethylbenzene concentration is based on the amount of ethylbenzene relative to the amount of $C_8$ aromatics in the aromatic formation effluent (and/or in an aromatic hydrocarbon feed stream derived from an aromatic formation effluent). In various aspects, the amount of ethylbenzene can be 3 wt % or less of the amount of $C_8$ aromatics in the aromatics formation effluent (and/or aromatic hydrocarbon feed stream), or 2 wt % or less, or 1 wt % or less. Another option for characterizing the ethylbenzene concentration is based on the amount of ethylbenzene relative to the total aromatics in the aromatic formation effluent (and/or aromatic hydrocarbon feed stream). In various aspects, the amount of ethylbenzene can be 5 wt % or less of the total amount of aromatics in the aromatics formation effluent (and/or aromatic hydrocarbon feed stream), or 2 wt % or less, or 1 wt % or less, or 0.5 wt % or less, or 0.1 wt % or less. Additionally or alternately, the amount of aromatics having $C_{2+}$ side chains can be characterized relative to the total aromatics in the aromatic formation effluent (and/or aromatic hydrocarbon feed stream). In various aspects, the amount of aromatics having $C_{2+}$ side chains can be 5 wt % or less of the total amount of aromatics in the aromatic formation effluent (and/or aromatic hydrocarbon feed stream), or 2 wt % or less, or 1 wt % or less, or 0.5 wt % or less, or 0.1 wt % or less. Additionally or alternately, the amount of methyl side chains can be characterized relative to the total amount of alkyl side chains for aromatics having side chains. In various aspects, for aromatic compounds having side chains, the amount of methyl side chains relative to the total amount of alkyl side chains can be at least 90%, or at least 95%, or at least 98%.

For the purpose of this description and appended claims the following terms are defined. The term "$C_n$" hydrocarbon wherein n is a positive integer, means a hydrocarbon having n number of carbon atom(s) per molecule. The terms "$C_{n+}$" hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The term "aromatics" means hydrocarbon molecules containing at least one aromatic core. The term "hydrocarbon" encompasses mixtures of hydrocarbon, including those having different values of n. The term "organic oxygenate" means molecules (including mixtures of molecules) having the formula $C_nH_{2n+1}OC_mH_{2m+1}$, wherein C, H, and O are carbon, hydrogen, and oxygen, respectively; n is an integer having a value $\geq 1$, e.g., in the range of from 1 to 4; and m is an integer having a value $\geq$ zero, e.g., in the range of from zero to 4. Examples of organic oxygenate include one or more of methanol, ethanol, dimethyl ether, and diethyl ether. The term "inorganic oxygenate" means oxygenate molecules that do not satisfy the specified formula for organic oxygenate. Examples of $C_{1+}$ inorganic oxygenate include one or more of aldehyde, carbon monoxide, and carbon dioxide.

In this description and appended claims, reference may be made to aromatics streams or fractions described as a $C_6$ aromatics stream or fraction, $C_7$ aromatics stream or fraction, $C_6$-$C_7$ aromatics stream or fraction, $C_8$ aromatics stream or fraction, $C_7$-$C_8$ aromatics stream or fraction, $C_9$ aromatics stream or fraction, or $C_9$+ aromatics stream or fraction. In this description and appended claims, each of these named types of streams or fractions is defined to have a concentration of the named aromatic component(s) of at least 50 wt %. Thus, a $C_6$ aromatics stream is defined herein as a stream containing at least 50 wt % of $C_6$ aromatic compounds. Optionally, the concentration of the named aromatic component(s) can be at least 75 wt %, or at least 90 wt %.

Processes for conversion of alkanes to aromatics, as described herein, can generally be characterized as either direct conversion processes or indirect conversion processes. Direct conversion processes are defined herein as processes where the alkane-containing feed is introduced into the reaction environment where aromatics are formed from non-aromatic compounds. Indirect conversion processes are defined herein as processes where the alkane-containing feed is introduced into a reaction stage different from the reaction stage where aromatics are formed. For example, a reaction scheme for first converting methane to methanol and then feeding the methanol into a reaction for aromatic formation corresponds to an indirect conversion process. It is noted that a reaction scheme could correspond to both a direct and an indirect conversion process if some aromatics are formed in a first process that receives the alkane-containing feed while additional aromatics are formed in a second process that receives an effluent from the first process as a feed. It is noted that subsequent methylation of an existing aromatic feed does not correspond to a process for formation of aromatics from non-aromatic compounds.

As used herein, an "aromatic formation" process refers to one or more processes that are used to convert aliphatic hydrocarbons (optionally in the presence of other components and/or co-feeds) to aromatics via an alkyl halide and/or alcohol intermediate. An aromatic formation process, based on a direct conversion process, may encompass those having only one reactor and/or reaction stage (although multiple stages could be included). An aromatic formation process based on an indirect conversion process will typically include multiple process stages or reaction environments, since the reaction for initial conversion of the alkanes occurs in a different reaction environment than the reaction for aromatic formation.

As used herein, the numbering scheme for the groups of the Periodic Table of the Elements is as disclosed in the current IUPAC version.

Feeds for Aromatic Formation Process

Two types of hydrocarbonaceous feeds can be used for formation of single ring aromatics with a reduced or minimized content of $C_{2-}$ side chains. One option for a feed is to use an alkyl halide and/or alcohol as the feed. Another option can be to use an alkane feed, and then convert the alkane to an alkyl halide, alcohol, or combination thereof. Optionally, but preferably, the alkyl halide can be a methyl halide. Optionally, but preferably, the alcohol can be methanol.

When the aromatics formation process is based on conversion of alkyl halides, representative feeds include those comprising at least 20 mol % of one or more $C_1$-$C_9$ alkyl halides relative to the total number of moles in the feed, or at least 35 mol %, or at least 50 mol %, or at least 60 mol %, or at least 70 mol %, or at least 80 mol %. Optionally, the feed further comprises diluent. Diluent present in the feed's source (e.g., water and/or $CO_2$ present in natural gas) and diluent added to the feed are within the scope of the invention. Diluent, when present, is typically included in the feed in an amount ≤60 wt % based on the weight of the feed, e.g., ≤50 wt %, such as ≤40 wt %, or ≤30 wt %, or ≤20 wt %, or ≤10 wt %. A feed constituent is diluent when it is substantially non-reactive under the specified aromatics formation reaction. Organic and inorganic diluents are within the scope of the invention. In some aspects, at least a portion of the alkyl halides in the feed can include methyl halides, e.g., ≥10 wt % methyl halides, or ≥20 wt %, or ≥40 wt %, or ≥60 wt %, or ≥80 wt %.

When the aromatics formation process is based on conversion of alcohols, representative feeds include those comprising at least 20 mol % of one or more $C_1$-$C_9$ alcohols relative to the total number of moles in the feed, or at least 35 mol %, or at least 50 mol %, or at least 60 mol %, or at least 70 mol %, or at least 80 mol %. Optionally, the feed further comprises diluent. Diluent present in the feed's source (e.g., water and/or $CO_2$ present in natural gas) and diluent added to the feed are within the scope of the invention. Diluent, when present, is typically included in the feed in an amount ≤60 wt % based on the weight of the feed, e.g., ≤50 wt %, such as ≤40 wt %, or ≤30 wt %, or ≤20 wt %, or ≤10 wt %. A feed constituent is diluent when it is substantially non-reactive under the specified aromatics formation reaction. Organic and inorganic diluents are within the scope of the invention. In some aspects, at least a portion of the alcohols in the feed can include methanol, e.g., ≥10 wt % methanol, or ≥20 wt %, or ≥40 wt %, or ≥60 wt %, or ≥80 wt %.

A variety of methods can be used for converting an alkane to an alkyl halide or an alcohol. For example, alkanes can be converted into syngas by hydrocarbon reforming. The molar ratio of $H_2$ to CO generated during reforming can depend on the type of reforming, such as higher ratios of $H_2$ to CO for steam reforming. The syngas can be produced by any convenient method, including conventional methods such as the partial oxidation of methane and/or the steam reforming of methane. Suitable methods include those described in U.S. Publication Nos. 2007/0259972 A1, 2008/0033218 A1, and 2005/0107481. The syngas can then be used to synthesize methanol using conventional processes.

The resulting syngas can then be converted to syngas-to-methanol and/or dimethyl ether (DME) and then the methanol and/or DME used in a methanol-to-aromatics conversion process. For example, the conversion of syngas to methanol (or other alcohols) can be carried out at very high selectivity using a mixture of copper, zinc oxide, and alumina at a temperature of 200° C. to 400° C. and pressures of 50-500 atm. In addition to $Cu/ZnO/Al_2O_3$, other catalyst systems suitable for methanol synthesis include $Zn/VCr_2O_3$, $Cu/ZnO$, $Cu/ZnO/Cr_2O_3$, $Cu/ThO_2$, $CoS_x$, $MoS_x$, Co—$MoS_x$, Ni—$MoS_x$, and Ni—Co—$MoS_x$.

Similarly, a variety of conventional methods are available for converting alkanes to alkyl halides. One example of an alkyl halide conversion process is shown in U.S. Publication 2013/0158324, which provides a process for conversion of alkanes (including methane) into alkyl bromides.

When the aromatics formation process is initiated by converting alkanes, representative alkane-containing feeds include those comprising at least 20 mol % of one or more $C_1$-$C_9$ alkanes relative to the total number of moles in the feed, or at least 35 mol %, or at least 50 mol %, or at least 60 mol %, or at least 70 mol %, or at least 80 mol %. Additionally or alternately, the alkane-containing feedstock can initially contain at least 50 mol % of one or more $C_1$-$C_9$ alkanes relative to the total number of moles of hydrocarbon in the feed, or at least 60 mol %, or at least 70 mol %, or at least 80 mol %. Optionally, the feed further comprises diluent. Diluent present in the feed's source (e.g., water and/or $CO_2$ present in natural gas) and diluent added to the feed are within the scope of the invention. Diluent, when present, is typically included in the feed in an amount ≤60 wt % based on the weight of the feed, e.g., ≤50 wt %, such as ≤40 wt %, or ≤30 wt %, or ≤20 wt %, or ≤10 wt %. A feed constituent is diluent when it is substantially non-reactive under the specified aromatics formation reaction. Organic and inorganic diluents are within the scope of the invention.

In some aspects, at least a portion of the alkanes in the feed can include methane, e.g., ≥10 wt % methane, or ≥20 wt %, or ≥40 wt %, or ≥60 wt %, or ≥80 wt %. Alternatively or in addition, the feed can comprise ethane, e.g., ≥1 wt % ethane, based on the weight of the feed, such as ≥5 wt %, or ≥10 wt %, or in the range of from 10 wt % to 70 wt %. Alternatively or in addition to the methane and/or ethane, the feed can contain $C_3$ and/or $C_4$ hydrocarbon e.g., (i) ≥20 wt % propane, such as ≥40 wt %, or ≥60 wt %, and/or (ii) ≥20 wt % butanes, such as ≥40 wt %, or ≥60 wt %. In some aspects, the feed can contain a reduced amount of $C_{5+}$ hydrocarbon, e.g., ≤20 wt %, such as ≤10 wt %, or ≤1 wt %. In such aspects, the feed can contain ≤10 wt % of $C_{6+}$ saturated hydrocarbon, e.g., ≤5 wt %.

Optionally, the feed comprises molecular hydrogen, e.g., ≥1 wt % molecular hydrogen based on the weight of the feed, such as ≥5 wt %. Optionally, the feed contains unsaturated $C_{2+}$ hydrocarbon, such as $C_2$-$C_5$ unsaturated hydrocarbon. When present, the amount of $C_{2+}$ unsaturated hydrocarbon (e.g., $C_2$-$C_5$ unsaturated hydrocarbon) is typically ≤20 wt %, e.g., ≤10 wt %, such as ≤1 wt %, or ≤0.1 wt %, or in the range of from 0.1 wt % to 10 wt %. More particularly, the feed is generally one that is substantially-free of aromatic hydrocarbon, where substantially-free in this context means an aromatic hydrocarbon content that is <1 wt % based on the weight of the feed, such as ≤0.1 wt %, or ≤0.01 wt %, or ≤0.001 wt %. Typically, the feed comprises a total of ≤10 wt % of impurities such as CO, $CO_2$, $H_2S$, and total mercaptan; e.g., ≤1 wt %, or ≤0.1 wt %.

Examples of Aromatic Formation Processes

An example of a suitable process for converting methanol and/or DME to aromatics can be conversion to gasoline (including aromatics) employing the MTG (methanol-to-gasoline) process. The MTG process is disclosed in the patent art, including, for example, U.S. Pat. Nos. 3,894,103; 3,894,104; 3,894,107; 4,035,430; and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because $C_{10+}$ olefin precursors are rapidly converted via hydrogen transfer to heavy polymethylaromatics and $C_4$ to $C_8$ isoparaffins under methanol conversion conditions.

More generally, conversion of methanol (and/or dimethyl ether) to aromatics can be performed using as a catalyst a composition of matter comprising a molecular sieve and a Group 8-14 element, or a molecular sieve and a combination of metals from the same group of the Periodic Table. The composition of matter can, optionally, further comprise phosphorus and/or lanthanum and/or other elements from Group 1-2 and/or Group 13-16 of the Periodic Table that provide structural stabilization. Many examples of conversion of methanols and/or olefins to aromatics are conventionally known, such as the processes described in U.S. Publication 2015/0175499, the entirety of which is incorporated herein by reference.

A suitable feed can be converted to aromatics by exposing the feed to a conversion catalyst under effective conversion conditions. General conversion conditions include a pressure of about 100 kPaa to about 2500 kPaa, or about 100 kPaa to about 2000 kPaa, or about 100 kPaa to about 1500 kPaa, or about 100 kPaa to about 1200 kPaa. The amount of feed (weight) relative to the amount of catalyst (weight) can be expressed as a weight hourly space velocity (WHSV). Suitable weight hourly space velocities include a WHSV of about 0.1 $hr^{-1}$ to about 20 $hr^{-1}$, or about 1.0 $hr^{-1}$ to about 10 $hr^{-1}$. A wide range of temperatures can be suitable, depending on the desired type of aromatics-containing product. Thus, temperatures of about 300° C. to about 600° C., or about 300° C. to about 450° C., or about 300° C. to about 400° C., or about 350° C. to about 550° C., or about 400° C. to about 600° C. can be suitable.

In some aspects, the conversion conditions can be selected to reduce or minimize the amount of non-aromatic $C_2$-$C_5$ compounds in the aromatic formation effluent. $C_2$-$C_5$ compounds, such as oxygenates, alkyl halides, and aliphatic hydrocarbons, can tend to crack under the conversion conditions. This can lead to increased formation of aromatics with $C_{2+}$ side chains. One option for reducing the amount of $C_2$-$C_5$ compounds in the aromatic formation effluent can be to operate the aromatic formation process at lower space velocities and/or at increased temperatures. Examples of lower space velocities include space velocities from 0.1 $hr^{-1}$ to 2.0 $hr^{-1}$, or 0.1 $hr^{-1}$ to 1.0 $hr^{-1}$, or 0.1 $hr^{-1}$ to 0.6 $hr^{-1}$. Examples of increased temperatures include temperatures of 400° C. to 600° C., or 450° C. to 600° C., or 500° C. to 600° C. Another option can be to select a catalyst for the aromatic formation process that reduces the amount of $C_2$-$C_5$ compounds in the aromatic formation effluent, such as a catalyst that is modified by addition of at least one element from Groups 2-14 of the periodic table.

Additionally or alternately, the feed to the aromatic formation process can be introduced using staged injection of the feed. Staged injection of feed for alkylation is described in U.S. Pat. No. 9,095,831, which is incorporated herein by reference. Briefly, staged injection involves introducing feed at multiple locations within a reactor relative to the direction of flow. Structures can be used in between the multiple locations to reduce or minimize at least one of gas phase back-mixing of the feed within the reactor, by-pass phenomena, and gas bubble size.

Generally, the process conditions for conversion of methanol to aromatics can be selected to produce $C_6$-$C_9$ aromatics. Higher and lower boiling range compounds can be separated from $C_6$-$C_9$ aromatics by distillation, as described in greater detail below. Although $C_{10}$ aromatics can potentially correspond to a single ring aromatic, $C_{10}$ aromatics can also correspond to naphthalene, which is not readily converted to xylene. However, to the degree that tetra-methylated $C_{10}$ aromatic compounds are present in a desired $C_6$-$C_9$ aromatics portion of an aromatics formation effluent, such tetra-methylated $C_{10}$ aromatics are not believed to reduce or minimize the other benefits described herein.

The selectivity for production of $C_6$, $C_7$, $C_8$, and/or $C_9$ aromatics provides one option for characterizing an aromatic formation process, e.g., the selectivity for production of $C_6$, $C_7$, $C_8$, and/or $C_9$ aromatics in the aromatics formation process's effluent. For example, the amount of particular aromatic hydrocarbon in the process effluent can be 40 wt % of the total aromatics in the effluent, or at least 50 wt %, or at least 60 wt %, or at least 70 wt %; or 20 wt % or less of the total aromatics in the effluent, or 10 wt % or less, or 5 wt % or less. The particular aromatic hydrocarbon can be one or more $C_6$ to $C_8$ aromatic hydrocarbon compounds, e.g., (i) $C_8$ aromatic hydrocarbon and/or (ii) $C_6$-$C_7$ aromatic hydrocarbon. In other aspects, the amount of $C_9$ aromatics in the aromatic formation effluent can be at least 40 wt % of the total aromatics, or at least 45 wt %, or at least 50 wt %. Additionally or alternately, the amount of $C_{9+}$ aromatics can be at least 50 wt % of the total aromatics in the aromatic formation effluent, or at least 55 wt %, or at least 60 wt %, or at least 65 wt %. Additionally or alternately, the amount of $C_8$ aromatics can be 30 wt % or less, or 25 wt % or less, or 20 wt % or less.

Another option for characterizing an aromatics formation effluent can be based on the selectivity for production of one or more particular aromatics relative to the total amount of aromatics in the process effluent. For example, the amount of ethylbenzene in the process effluent can be 5 wt % or less relative to the total $C_8$ aromatics in the effluent, or 4 wt % or less, or 3 wt % or less. Additionally or alternately, the aromatics with $C_{2+}$ side chain substitution in the effluent can be 10 wt % or less relative to the total single ring $C_7$-$C_{10}$ aromatics in the effluent, or 8 wt % or less, or 6 wt % or less, or 4 wt % or less, or 2 wt % or less. Additionally or alternately, the aromatics with $C_{2+}$ side chain substitution in the effluent can be 5 wt % or less relative to the total aromatics in the effluent, or 3 wt % or less, or 2 wt % or less, or 1 wt % or less. In aspects where para-xylene is separated from other $C_8$ aromatics, a reduced or minimized content of ethylbenzene can allow for use of a liquid isomerization process as part of a para-xylene recovery loop and/or can reduce or minimize the amount of purge required from such a liquid isomerization process. Still another option can be to characterize an aromatics formation effluent based on a ratio of alkyl-substituted aromatics having only methyl side chains versus aromatics having at least one $C_{2+}$ side chain.

In various aspects, the (weight) ratio of alkyl-substituted aromatics having only methyl side chains versus aromatics having at least one $C_{2+}$ side chain can be at least 5, or at least 10, or at least 12, or at least 14, or at least 15, such as up to 25 or more, or up to 50 or more. Yet another option can be characterizing the amount of certain $C_9$ aromatics, such as para-methyl-ethylbenzene and/or isopropylbenzene. In various aspects, the amount of para-methyl-ethylbenzene and/or isopropylbenzene in the aromatic formation effluent can be 0.1 wt % or less of the total aromatics, or 0.05 wt % or less.

The conditions for conversion of alkyl halides to aromatics can be similar in some respects to those for conversion of oxygenates to aromatics. With regard to the conversion catalysts, the catalyst may be any of a variety of suitable materials for catalyzing the conversion of the alkyl bromides to higher molecular weight hydrocarbons. Examples of suitable catalysts include a fairly wide range of materials that have the common functionality of being acidic ion-exchangers and that correspond to microporous and/or mesoporous crystalline structures. Optionally, the catalyst can have a zeolite framework structure, such as a zeolite framework structure as recognized by the International Zeolite Association. An example of a catalyst having a zeolite framework structure is a catalyst having the MFI framework structure. A catalyst having a zeolite framework structure can be a zeolite (i.e., an aluminosilicate) or can include heteroatoms other than silicon and aluminum in the framework structure. Optionally, the catalyst can further include a binder. Optionally, the catalyst may also contain between about 0.1 wt % to about 1 wt % Pt or about 0.1 wt % to about 5 wt % Pd.

In some aspects, suitable conditions for conversion of alkyl halides to aromatics can correspond to conditions similar to those identified in U.S. Publication 2013/0158324. For example, suitable conditions can include exposing a feed containing HBr and alkyl bromide (such as a mixture of alkyl bromides) to an MFI framework structure catalyst, such as ZSM-5. The conversion conditions can include a temperature of about 300° C. to about 450° C.

In other aspects, suitable conditions can correspond to conditions similar to those identified in a journal article from Applied Catalysis A: General, Vol. 36, pp. 99-107 (2009). For example, suitable conditions can include exposing a feed of $CH_3Br$ at a temperature of 300° C. to 450° C. to a catalyst including 5 wt % PbO on ZSM-5. In such aspects, the reaction conditions can be selective for generating $C_9$ and $C_{10}$ single ring aromatics relative to production of $C_6$ and $C_7$ aromatics. $C_9$ and/or $C_{10}$ single ring aromatics can then be converted to xylenes by transalkylation.

Initial Separation Process for Separation of Aromatic Formation Effluent

The effluent from the aromatic formation process can be conducted to a first separation process for separation of one or more streams or fractions from the effluent. The initial or first separation process can include one or more separation stages based on boiling point (distillation) differences within the effluent. Optionally, for feeds including a substantial portion of $C_{6+}$ alkanes, a solvent separation stage may also be provided for separation of $C_{6+}$ alkanes from $C_{6+}$ aromatic products.

Generally, the effluent from aromatic formation can include aromatics, unreacted feed, and optionally additional non-aromatic reaction products. Most of the components in the effluent can be conveniently separated based on distillation methods. The particular types of streams formed during separation can be dependent on the nature of the aromatic formation process.

In some aspects, the effluent from an aromatic formation process can include substantial amounts (such as more than 10 vol %, or more than 20 vol %) of $C_6$, $C_7$, and $C_8$ aromatics, or $C_6$, $C_7$, $C_8$, and $C_{9+}$ aromatics. In such aspects, a distillation can allow for separation from the aromatic formation effluent of at least a $C_6$-$C_7$ aromatics stream, a $C_8$ aromatics stream, a (optional) $C_{9+}$ aromatics stream, optionally an unreacted feed stream and/or a hydrogen stream, and optionally one or more additional non-aromatic reaction product streams. Depending on the nature of the separation process, the $C_9+$ aromatics stream or another product stream can alternatively correspond to a remaining portion of the effluent after separation of other streams. As defined previously, the named aromatic component ($C_6$-$C_7$; $C_8$; $C_{9+}$) for a stream corresponds to at least 50 wt % of the aromatic content in the stream, or at least 75 wt %, or at least 90 wt %. The $C_8$ stream (or at least a portion of the $C_8$ stream) can be sent to a subsequent separation process for separation of a para-xylene enriched stream. The $C_6$-$C_7$ stream (or at least a portion of the $C_6$-$C_7$ stream) can be sent to a methylation process for conversion of at least a portion of the $C_6$-$C_7$ components to $C_8$ components. The $C_{9+}$ stream can be withdrawn from the reaction system, exposed to a dealkylation process to generate additional benzene for introduction into the methylation stage, exposed to a transalkylation process to generate additional $C_8$ aromatics for introduction into the xylene separation zone, and/or handled in any other convenient manner Optionally, a portion of the unreacted feed can be recycled to the aromatic formation process.

In some alternative aspects, it may be desirable to separate a $C_6$ stream and a $C_7$ stream from the aromatic formation effluent to allow for removal of a portion of the benzene stream as a product. Additionally or alternately, this can be desirable during production of naphtha boiling range fuels or fuel components, so that at least a portion of the benzene can be selectively methylated to form toluene.

In other aspects, the output from the effluent from the aromatic formation process may contain substantial amounts of $C_6$ and $C_7$ aromatics, while having a reduced or minimized content of $C_8$ and/or $C_{9+}$ aromatics. In such aspects, a distillation can allow for separation from the aromatic formation effluent of at least a $C_6$ aromatics (i.e., benzene) stream, a $C_7$ aromatics stream, an unreacted feed stream and/or a hydrogen stream, and optionally a stream of non-aromatic reaction products. In yet other aspects, the effluent from the aromatic formation process may contain substantial amounts of $C_6$ aromatics, methane (or other unreacted feed), and hydrogen, while having a reduced or minimized amount of other aromatic components. In such aspects, the initial separation stage can separate at least a $C_6$ aromatics stream, an unreacted feed stream, and/or a hydrogen stream from the aromatic formation effluent.

Methylation of Aromatics

At least a portion of a $C_6$ stream, $C_7$ stream, or $C_6$-$C_7$ stream separated from the aromatic formation effluent in the first separation process can optionally be used as a product stream, as both benzene and toluene are commercially valuable. Another option can be to use at least a portion of a $C_6$ stream, $C_7$ stream, or $C_6$-$C_7$ stream separated from the aromatic formation effluent as a feed for a methylation process. A methylation process can form $C_8$ compounds by reacting $C_6$ and/or $C_7$ compounds with a methylating agent, such as methanol, dimethyl ether (DME), methyl bromide, and/or methyl chloride. Methylation processes typically provide a high selectivity for forming xylenes in preference to ethylbenzene. An example of a process for the selective production of para-xylene by exposing benzene and/or toluene to methanol under effective catalytic conditions is described in U.S. Pat. No. 8,344,197, which is incorporated herein by reference. Additionally or alternately, a methylation process can be used for production of toluene from benzene.

Temperature is an important parameter in the reaction of benzene and/or toluene with a methylating agent. Because temperatures between 450° C. and 700° C. are beneficial for improving or maximizing conversion, the aromatic feed and methylating agent feed are preheated before being supplied to the methylation process, with the exothermic heat generated by the methylation reaction generally being sufficient to maintain the reaction temperature at the desired value. In practice, however, there are limits on the temperatures to which the different feeds can be preheated. For example, in the case of the benzene/toluene feed, the preheating temperature is limited by the coking rates in the preheater which, depending on factors such as heat flux, stream composition and heat transfer surface metallurgy, will generally be about 550° C. In the case of the methylating agent feed, decomposition to carbon oxides, hydrogen, and methane will generally limit the preheating temperature to about 220° C.

Generally, the conditions employed in a methylation process can include a temperature between 450° C. and 700° C., or about 550° C. to about 650° C.; a pressure between 14 psig and 1000 psig (between 100 and 7000 kPa), or between 10 psig and 200 psig (between 170 and 1480 kPa); a molar ratio of aromatic to methanol in the reactor charge of at least 0.2, such as from 2 to 20; and a weight hourly space velocity ("WHSV") for total hydrocarbon feed to the reactor(s) of 0.2 to 1000 $hr^{-1}$, or 0.5 to 500 $hr^{-1}$ for the aromatic reactant, and 0.01 to 100 $hr^{-1}$ for the methylating agent, based on total catalyst in the reactor(s).

The methylation process employed herein can employ any aromatic feedstock comprising toluene and/or benzene. Optionally, the aromatic feed can contain at least 90 wt %, especially at least 99 wt %, of benzene, toluene or a mixture thereof. The composition of the methylating agent feed is not critical. Optionally, it can be beneficial to employ feeds containing at least 90 wt %, especially at least 99 wt %, of a methylating agent.

The catalyst for methylation can be a porous crystalline material. The porous crystalline material is preferably a medium-pore size aluminosilicate zeolite. Medium pore zeolites are generally defined as those having a pore size of about 5 to about 7 Angstroms, such that the zeolite freely sorbs molecules, such as n-hexane, 3-methylpentane, benzene, and para-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Transalkylation of Aromatics

In various aspects, at least a portion of a $C_{9+}$ stream can be separated from the aromatic formation effluent as a feed for a transalkylation process. Conventionally, a transalkylation process can form $C_8$ compounds by reacting the $C_{9+}$ compounds with $C_6$ and/or $C_7$ compounds and hydrogen.

Transalkylation processes can typically include exposing the feed for transalkylation to a catalyst with activity for converting aromatics with $C_{2+}$ side chains into dealkylated aromatics. Such catalytic activity can also have the effect of removing methyl side chains from aromatics, which can result in a loss of xylene yield from a transalkylation process. The removal of alkyl side chains can also present difficulties, as many conventional methods for dealkylation may require gas phase processing conditions, as opposed to processing under conditions where the continuous fluid phase is a liquid.

Generally, a suitable transalkylation catalyst can be a molecular sieve that has a constraint index of 1-12, optionally but preferably less than 3. The constraint index can be determined by the method described in U.S. Pat. No. 4,016,218, which is incorporated herein by reference with regard to the details of determining a constraint index. Examples of suitable molecular sieves include, but are not limited to, 10-member ring and 12-member ring molecular sieves, such as molecular sieves having the framework type corresponding to ZSM-5, ZSM-11, ZSM-23, ZSM-48, ZSM-35, ZSM-12, ZSM-3, ZSM-4, ZSM-18, NU-87, ZSM-20, mordenite, zeolite Beta, zeolite Y, and USY.

In various aspects, a transalkylation process can be operated in an improved manner when the transalkylation feed includes a reduced or minimized amount of (single-ring) aromatics having $C_{2+}$ side chains. In such aspects, the need for a transalkylation catalyst (such as a transalkylation catalyst system) that includes dealkylation activity can be reduced or minimized. For example, this can allow the use of a transalkylation catalyst with a content of supported Group 6-10 metals or Group 8 metals (optionally in the form of supported metal oxides) of about 1 wt % or less, or about 0.1 wt % or less, or about 0.001 wt % or less. A Group 6-10 metal or Group 8 metal can be beneficial for providing hydrogenation functionality during dealkylation. For a feed that requires little or no dealkylation, this functionality is not required.

Additionally or alternately, a transalkylation catalyst (such as a transalkylation catalyst system) can be used that has a reduced or minimized activity for dealkylation. The Alpha value of a catalyst can provide an indication of the activity of a catalyst for dealkylation. In various aspects, the transalkylation catalyst can have an Alpha value of about 10 or less, or about 1 or less. The Alpha value test is described in U.S. Pat. No. 3,354,078, which is incorporated herein by reference with regard to the description of performing an Alpha value test. The conditions used for determining an Alpha value as described herein correspond to the conditions specified in Journal of Catalysis, Vol. 61, p. 395.

Additionally or alternately, the transalkylation conditions can correspond to conditions where the continuous fluid phase is a liquid. This is in contrast to typical gas phase transalkylation conditions, where the continuous fluid phase is a gas. It is noted that in gas phase transalkylation conditions, a plurality of liquid phases may form in the vicinity (i.e., on the surface) of catalyst particles. However, such liquid phases do not form a continuous liquid phase.

Generally, the conditions employed in a transalkylation process can include a temperature between 100° C. and 1000° C., or about 300° C. to about 500° C.; a pressure of 790 kPaa to 7000 kPaa, or 2000 kPaa to 3000 kPaa; an H$_2$:hydrocarbon molar ratio of 0.01 to 20, or 0.1 to 10; and a weight hourly space velocity ("WHSV") for total hydrocarbon feed to the reactor(s) of 0.1 to 100 hr$^{-1}$, or 1 to 20 hr$^{-1}$.

The methylation process employed herein can employ any aromatic feedstock comprising toluene and/or benzene. Optionally, the aromatic feed can contain at least 90 wt %, especially at least 99 wt %, of benzene, toluene, or a mixture thereof. The composition of the methylating agent feed is not critical. Optionally, it can be beneficial to employ feeds containing at least 90 wt %, especially at least 99 wt %, of a methylating agent.

The catalyst for methylation can be a porous crystalline material. The porous crystalline material is preferably a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene, and para-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Second Separation Zone

The methylation process and/or transalkylation process can produce an effluent that can be separated to form one or more output streams based on boiling point or distillation. In aspects including a methylation process, a first output stream separated from a methylation effluent can be an unreacted C$_6$-C$_7$ stream (possibly including C$_7$ compounds that formed due to methylation of C$_6$), which can be at least partially recycled to the methylation. A second output stream separated from the methylation effluent can correspond to a lower boiling point stream, including unreacted methanol (or other methylating agent) and other C$_5$– reaction products. A third output stream separated from the methylation effluent can correspond to a C$_8$ aromatics stream. Optionally, one of the first output stream, second output stream, or third output stream can correspond to a remaining portion of the methylation effluent after separation of other output streams.

In aspects including a transalkylation process, a first output stream separated from a transalkylation effluent can be a C$_6$-C$_7$ stream (possibly including unreacted C$_6$-C$_7$ compounds), which can be at least partially recycled to the transalkylation. A second output stream separated from the transalkylation effluent can correspond to C$_{9+}$ compounds (possibly including unreacted C$_{9+}$ compounds). A third output stream separated from the transalkylation effluent can correspond to a C$_8$ aromatics stream. Optionally, one of the first output stream, second output stream, or third output stream can correspond to a remaining portion of the methylation effluent after separation of other output streams.

Although an aromatic formation process, a methylation process, and/or a transalkylation process can generate similar product streams (i.e., a C$_8$ aromatics stream, C$_6$-C$_7$ product stream), in various aspects different separation processes can be employed for separation of the methylation effluent, the transalkylation effluent, and/or the aromatic formation effluent. While it is possible that the methylation effluent, the transalkylation effluent, and/or the aromatic formation effluent could have substantially the same ratios of C$_8$ products in the respective C$_8$ aromatics streams, more typically the C$_8$ aromatics streams produced from the aromatic formation process and the methylation process will have different compositions. This can include differences in both the concentration of para-xylene and the concentration of ethylbenzene. The differences in the concentration of para-xylene between C$_8$ aromatics streams can be exploited to provide an improved para-xylene separation process. Streams having a greater para-xylene concentration, e.g., the C$_8$ aromatics stream conducted away from the second separator can be kept segregated from streams having a lesser para-xylene concentration. Processing the segregated streams in distinct separation stages and/or in distinct zones within a separation stage has been found to beneficially (i) increase the efficiency of para-xylene separation, (ii) increase para-xylene yield, and/or (iii) decrease the size, capacity, and/or complexity of the xylene separation stages and zones compared to separations that are carried out with the streams combined.

One option for performing distinct separations on the effluents from the aromatic formation process, the methylation process, and/or the transalkylation process can be to use a divided wall column separator. Conventional divided wall column separators can be used, e.g., those that include separate volumes and a common volume. The separate volumes in the divided wall column separator are divided by a wall, with the height of the wall being selected so that products having a sufficiently low boiling range can enter a common volume of the separator. This can allow for formation of multiple high boiling range products while generating a single low boiling range output. During operation, two (or more) segregated streams can be each introduced into a separated or distinct volume of the divided wall column separator. As the effluent is distilled, the higher boiling portions of the streams remain segregated due to the dividing wall. The lower boiling portions can travel up the column of the separator into the common volume, where one or more common lower boiling fractions can be removed. The wall in the separator can provide any convenient configuration for the separated or otherwise segregated volumes. For example, the wall can correspond to a chord (such as a diameter) that bisects the typically circular shaped distillation column, or a wall that forms concentric separated volumes.

Xylene Isomerization and Separation

Due to similarities in the boiling points of the various C$_8$ aromatic isomers, distillation is not an effective method for separation of para-xylene from other xylenes and/or ethylbenzene. Instead, para-xylene is typically separated from a C$_8$ aromatic fraction or stream by other convenient methods, such as by selective adsorption or crystallization. U.S. Pat. Nos. 5,750,820 and 8,529,757 (each of which is incorporated herein by reference in its entirety) describe selective adsorption methods, which can be referred to as a simulated moving bed. The selective adsorption or crystallization can result in formation of a para-xylene enriched product stream and a para-xylene depleted stream that contains other C$_8$ isomers. The para-xylene depleted stream can be used as a feed for a xylene isomerization process, which can isomerize at least a portion of the other C$_8$ isomers to form para-xylene.

The isomerized product can then undergo further separation to recover additional para-xylene.

In the separation and isomerization loop described above, ethylbenzene can act as an inert contaminant that cannot be readily isomerized. One option for ethylbenzene removal is by dealkylation to benzene and ethane. This can be undesirable due to operating requirements of the dealkylation reaction (typically a gas phase process) and the downgrade of part of the molecule to fuel gas value. For aspects where liquid phase isomerization is used, a purge can be included in a separation and isomerization loop in order to prevent excessive buildup of ethylbenzene concentration. While such a purge is effective for preventing excessive ethylbenzene concentrations, a portion of $C_8$ xylene isomers is also lost in the purge stream. By using an aromatics feed with a reduced or minimized ethylbenzene content, the volume of the purge stream for operating the separation and isomerization loop can be reduced, leading to increased para-xylene yield.

A reduced purge stream can be characterized based on the weight of the purge stream relative to the weight of para-xylene product. This can be referred to as a separation purge ratio. In various aspects, providing a $C_8$ aromatics stream with a reduced or minimized ethylbenzene content to a xylene separation and isomerization loop can allow the loop to be operated with a separation purge ratio of 0.2 or less, or 0.15 or less, or 0.1 or less. It is noted that for a $C_8$ input stream with a reduced ethylbenzene content, an alternative to operating with a low separation purge ratio can be to perform the xylene separation under relaxed conditions that are less energy intensive.

Still another benefit of a reduced ethylbenzene content in a $C_8$ aromatics feed to a xylene separation and isomerization loop can be the reduced or minimized formation of para-methyl-ethylbenzene. If ethylbenzene is present in a xylene isomerization process, the isomerization process can convert a portion of the ethylbenzene to para-methyl-ethylbenzene. During para-xylene separation, para-diethylbenzene is often used as a displacement feed for removal of para-xylene from the separator. The para-diethylbenzene has a sufficiently distinct boiling point that it can be readily separated from para-xylene. For this type of system, para-methyl-ethylbenzene is a contaminant that can be difficult to separate from both para-xylene and para-diethylbenzene. Avoiding the initial formation of para-methyl-ethylbenzene can allow for improved purity for the resulting para-xylene product from xylene separation and/or can relax the separation conditions during a subsequent separation for removal of contaminants from the para-xylene product.

Xylene Separation (Third Separation Zone)

The description below describes the operation of a simulated moving bed based on the simple conceptual example of having a number of zones equal to the minimum number needed to show the different simulated moving bed processes at the same time. Those of skill in the art will recognize that more generally any number of zones can be included in a simulated moving bed separator. Generally, any convenient number of feed and/or output locations can be provided for the simulated moving bed. During operation, the different input streams and output streams for the simulated moving bed can be rotated through the feed and/or output locations to simulate the effect of having a moving bed separator.

In aspects where $C_8$ aromatic streams or fractions of varying para-xylene content are available, the $C_8$ output streams can be introduced into the simulated moving bed as separate feeds at different relative locations. For example, the effluent from the xylene isomerization process can be introduced at first location as would conventionally be expected. For the $C_8$ streams derived from the aromatic formation effluent and/or the methylation effluent, an input location downstream from the first location can be selected based on the para-xylene content of each respective effluent. This can optionally allow the $C_8$ stream separated from the aromatic formation effluent and/or the methylation effluent and/or the transalkylation effluent to be introduced into the simulated moving bed separator at a downstream location where the para-xylene concentration at the input location roughly matches the para-xylene content in the aromatic formation affluent or methylation effluent. This can reduce or minimize the required volume for the separator, as the $C_8$ streams with higher para-xylene concentration can be introduced at separate locations in the simulated moving bed. This can reduce the volume of input flows with lower para-xylene purity, which can require increased bed volume and/or energy to separate.

A xylene separation process can include any convenient number of feed input and/or output locations, with 4 to 30 locations being typical. For example, for a xylene separation process that includes 24 input locations, the isomerized effluent from the xylene isomerization reactor can be introduced into the first location. A $C_8$ aromatic stream separated from the aromatic formation effluent, the transalkylation effluent, and/or the methylation effluent can then be introduced at any other convenient location based on the percentage of para-xylene in the $C_8$ stream.

Additionally or alternately, a portion of the aromatic formation effluent and/or the methylation effluent can be used a flush stream for the input lines to the simulated moving bed. Because the entry and exit locations of the various streams in a simulated moving bed are constantly changing, the input and output lines for the simulated moving bed can contain streams of various purity levels. To avoid mixing a higher purity stream with a lower purity stream, flushing of the input and output lines can be performed. For example, when flushing an output line prior to withdrawal of high purity para-xylene product from the simulated moving bed, it is beneficial to first flush the stream with an intermediate purity stream followed by a flush stream having a para-xylene concentration comparable to the desired output. The higher para-xylene concentrations in an aromatic formation effluent and/or a transalkylation effluent and/or a methylation effluent can be suitable for use as an intermediate purity stream during flushing of the input and/or output lines.

A suitable adsorption apparatus or system might first permit adsorption of a product comprising the desired component(s) by the solids and later treat the solids to cause them to release the product and permit recovery of this product. Such an adsorption apparatus or system might comprise a "moving-bed" which permits movement of a tray or bed of the solids through a chamber, such that at different locations, the solid is subjected to different steps of an adsorption process, e.g., adsorption, purification, and desorption. These steps are defined in greater detail below. Nevertheless, moving the solids through an adsorption apparatus may be difficult and involve complex machinery to move trays or beds. It also may result in loss of the solids by attrition. To avoid these problems, some adsorption apparatus and systems have been designed to "simulate" moving the tray(s) or bed(s) to the locations, e.g., zones, of different steps of an adsorption process. Simulation of the movement of the tray(s) or bed(s) may be accomplished by use of a system of conduits which permits directing and redirecting the streams of fluids into the chamber at different zones at different times. As these stream changes occur, the solids are employed in different steps in an adsorption process as though the solids were moving through the chamber.

The different zones within an adsorption apparatus or system are defined by the particular step of the adsorption process performed within each zone, e.g., (1) an adsorption step in the adsorption zone; (2) a purification step in the purification zone; (3) a desorption step in the desorption zone. These terms have the same meaning as the description of these terms from U.S. Pat. No. 5,750,820. Briefly, in the adsorption zone, the input fluid comes into contact with the adsorbent material, and the desired component(s) are adsorbed by the adsorbent material. After adsorption, a purification stream is fed into the adsorbent material to flush the unwanted components from the adsorbent material, e.g., from within and from the interstitial areas between the solids. This results in a raffinate stream containing unwanted components that can be flushed from the purification zone. After the solids have been subjected to the purification stream, the stream in the conduit(s) may again be changed to introduce a desorbent steam (such as a high purity para-xylene stream) into the chamber to release the product.

Within each of the above zones, multiple inputs and/or outputs may also be present. For example, in the adsorption zone a first input stream can correspond to a lower concentration para-xylene stream. A second input stream can also be introduced within the adsorption zone, but at a downstream location where the concentration profile of para-xylene in the adsorption zone roughly matches the concentration of para-xylene in the second input stream.

Figure 4:
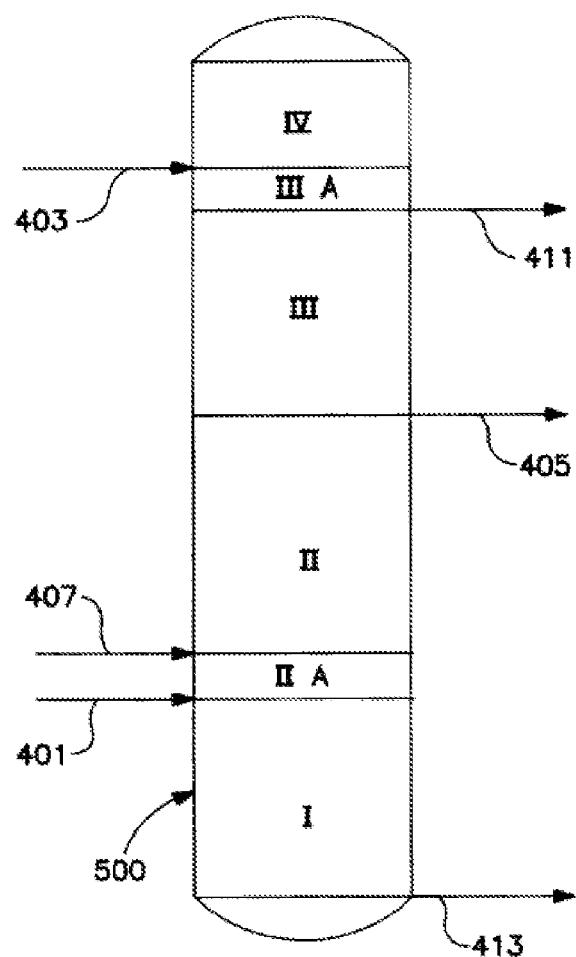
FIG. 4 schematically shows an example of a simulated moving bed separator.

FIG. 4 schematically shows an example of the presence of the various adsorption, desorption, and purification zones within a simulated moving bed. The zones shown in FIG. 4 represent the location of the zones at a particular instant in time. Rather than moving catalyst through these various zones, the inputs and outputs to the simulated moving bed can be varied so that the zones move relative to the catalyst instead of having the catalyst move relative to the zones. In FIG. 4, zone I corresponds to an adsorption zone, zone II corresponds to a purification zone, zone III corresponds to a desorption zone, and zone IV corresponds to a buffer zone to maintain separation between the desorption zone and the adsorption zone. It is noted that FIG. 4 also shows sub-zones IIA, IIB, and IIIA. These additional sub-zones represent additional feed entry and/or output exit locations. In various aspects, any convenient number of additional input and/or output locations can be used, to allow for additional input streams, additional flush streams, or additional output streams from a simulated moving bed.

In FIG. 4, chamber 500 is fed by feed fluid communication conduit 401 (corresponding to the input for adsorption zone I), desorbent fluid communication conduit 403 (corresponding to a high purity para-xylene stream for extraction of product from desorption zone III), flushing fluid communication conduit 407, and secondary flushing fluid communication conduit 409. Extract fluid communication conduit 405 (corresponding to the desired high purity para-xylene product), flushing fluid communication conduit 411, and raffinate fluid communication conduit 413 (corresponding to a para-xylene depleted output stream) lead from chamber 500. The input stream in conduit 401 can correspond to, for example, the output from the para-xylene isomerization stage. The flushing fluids introduced by conduits 407 and 409 can correspond to input streams having an intermediate para-xylene concentration relative to the concentration of the input stream in conduit 401 and the extract stream in conduit 405. These flushing streams can drive unwanted components from the bed so that a stream with increased para-xylene concentration can subsequently be extracted from the bed. The higher para-xylene concentration streams generated from aromatic formation and/or methylation can be introduced here, or they can be introduced at still other locations within the simulated moving bed based on the concentration of the streams relative to the concentration profile in the simulated moving bed. Flushing output 411 corresponds to an intermediate concentration output stream relative to the concentration of the input stream in conduit 401 and the extract stream in conduit 405.

Xylene Isomerization

Typically xylene streams found in chemical or petrochemical plants also contain ethylbenzene. Conventional isomerization technologies operating at high temperatures (e.g., 400° C.) in vapor phase isomerize the xylenes and dealkylate ethylbenzene to benzene. Other vapor-phase isomerization technologies convert ethylbenzene to xylenes in addition to xylene isomerization. There are also liquid-phase isomerization technologies.

For the methods described herein, both vapor phase isomerization and liquid phase isomerization can be suitable for isomerization of the para-xylene depleted stream from a para-xylene separation process. For aromatic formation processes, other than naphtha reforming and/or pyrolysis, a $C_8$ aromatics stream separated from the aromatic formation process can have a reduced ethylbenzene content. In some aspects, the reduced amount of ethylbenzene in $C_8$ aromatics streams separated from an aromatic formation effluent and/or methylation effluent can allow for reduced severity during vapor phase isomerization. In some aspects, the reduced amount of ethylbenzene in $C_8$ aromatic streams separated from the aromatic formation effluent and/or methylation effluent can allow for use of liquid phase isomerization for some or all of the isomerization of the para-xylene depleted stream from the para-xylene separation stage.

U.S. Pat. No. 8,697,929 describes an example of a liquid phase isomerization system, the entirety of which is incorporated herein by reference. Briefly, liquid phase isomerization of xylenes can be performed at a temperature of less than 295° C. and a pressure sufficient to maintain the xylenes in liquid phase. In embodiments, the process utilizes a catalyst comprising a zeolite, preferably at least one selected from the group consisting of ZSM-5 and MCM-49. In embodiments, the process utilizes a catalyst comprising ZSM-5, along with a binder, or the ZSM-5 may be self-bound. Optionally, the catalyst can be characterized by one or more of the following characteristics: the ZSM-5 is in the proton form (HZSM-5); the ZSM-5 has a crystal size of less than 0.1 microns; the ZSM-5 has a mesoporous surface area (MSA) greater than 45 $m^2/g$; the ZSM-5 has a zeolite surface area (ZSA) to mesoporous surface area (MSA) ratio of less than 9; a silica to alumina weight ratio in the range of 20 to 50.

In embodiments, very low level of by products are produced, such as less than 1 wt % or preferably less than 0.5 wt % of by-products selected from non-aromatic compounds, benzene and $C_9$+ aromatics, and mixtures thereof.

The liquid phase isomerization process comprises contacting a feedstream comprising $C_8$ aromatic hydrocarbons with a catalyst suitable for isomerization at a temperature below 295° C., preferably below 280° C., and at a pressure sufficiently to keep the reactant in liquid phase. One of skill in the art would be able to determine other operating characteristics, such as a lower temperature, within which the present invention may be practiced. Lower limits may be, for instance, above 180° C., or 190° C., or 200° C., or 210° C., and the like. The flow rate can be selected by one of ordinary skill in the art in possession of the present disclosure, but may advantageously be selected within the range from 0.1 to 100 hr$^{-1}$ WHSV, preferably from 0.5 to 20 hr$^{-1}$ WHSV, and more preferably from 1 to 10 hr$^{-1}$ WHSV.

Example 1—Conversion of Methanol to Aromatics with Low Content of $C_{2+}$ Side Chains Table 1 shows results from conversion of methanol to aromatics in the presence of ZSM-5 catalysts with about 1 wt % Zn and about 1 wt % P on the catalyst. The conversion was performed at a temperature of about 450° C., a pressure of about 15 psig, and weight hourly space velocities of methanol relative to catalyst of 0.5 hr$^{-1}$ to 2.0 hr$^{-1}$. In addition to overall yields, Table 1 includes the ratio of the number of methyl groups per ring in the product aromatics, the percentage of aromatics having $C_{2+}$ side chains, and the ratio of aromatics having only methyl side chains to aromatics having $C_{2+}$ side chains. Table 1 also shows the relative yield of ethylbenzene compared to other $C_8$ aromatics.

ethylbenzene in the xylene separation and isomerization loop. Isomerization feed 506 is then passed into xylene isomerization reactor 507. Optionally, xylene isomerization reactor 507 can correspond to a reactor that operates under liquid phase isomerization conditions. The isomerization product 508 is recycled to the para-xylene separator 502, either separately or by combination with the feed 501.

Figure 5:
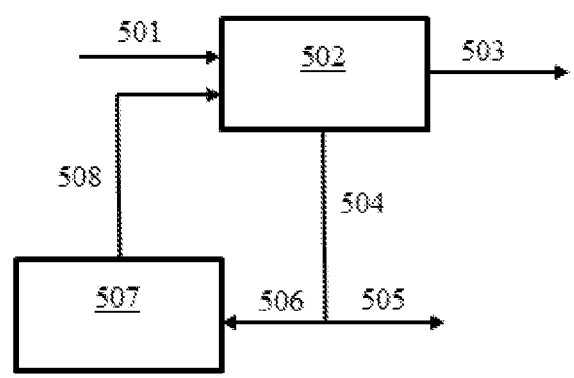
FIG. 5 schematically shows a simplified example of a xylene separation and isomerization loop.

Using the simplified configuration shown in FIG. 5, calculations were performed to determine the impact of reduced ethylbenzene concentrations on the relative weight of purge stream 506 and para-xylene product stream 503. In the calculations, feed 501 corresponded to a feed containing 100% of $C_8$ compounds, with the ethylbenzene concentration shown in Table 2. An ethylbenzene tolerance within the loop was then set at various values. A feed input weight per unit time of 1000 was used to simplify understanding the results. Table 2 shows the purge 506 stream as a percentage of the para-xylene depleted raffinate stream 504, the weight per unit time of the purge stream 506, and the weight per unit time of the para-xylene product 503.

TABLE 1

Methanol Conversion to Mono- and Poly-Methylated Aromatics

|  | 450 C. Fresh 1% Zn 1% P ZSM-5 | 4 h Steamed 1% Zn/1% P ZM5 | 4 h Steamed 1% Zn/1% P ZM5 | Example CCR Reformate |
|---|---|---|---|---|
| Pressure (psig) | 15.00 | 15.00 | 15.00 |  |
| Temperature (C.) | 450.00 | 450.00 | 450.00 |  |
| WHSV (h-1) | 2.00 | 0.50 | 1.00 |  |
| MeOH conversion (%) | 100 | 100 | 100 |  |
| Overall Yields |  |  |  |  |
| Olefins | 6.3% | 3.4% | 6.0% |  |
| Paraffins | 25% | 27% | 30% |  |
| Aromatics | 60% | 61% | 57% |  |
| Substituted benzenes yield | 59.4% | 59.4% | 55.6% |  |
| Methyl:Ring Ratio | 1.51 | 1.39 | 1.46 | 1.25 |
| % of side chain C that is ethyl+ | 6.37% | 5.36% | 6.23% | 26.22% |
| % of side chain C that is methyl | 93.63% | 94.64% | 93.77% | 73.78% |
| Ratio C ethyl+:methyl side chains | 14.69 | 17.64 | 15.05 | 2.81 |
| A8 yield | 21% | 20% | 19% |  |
| EB % of A8s | 3.4% | 3.0% | 3.4% | 28.2% |

As shown in Table 1, formation of aromatics by conversion of methanol can produce aromatics products with high selectivity for forming aromatics with only methyl side chains. As a result, forming aromatics by conversion of methanol can produce aromatics with low ethylbenzene content as well as a low content of $C_{9+}$ single-ring aromatics having $C_{2+}$ side chains.

Example 2—Purge Ratio for Xylene Separation and Isomerization Loop

FIG. 5 shows a schematic example of a xylene separation and isomerization loop. In FIG. 5, a feed 501 corresponding to a $C_8$ aromatics stream is introduced into a para-xylene separator 502. Para-xylene separator 502 forms a para-xylene product stream 503 and a para-xylene depleted raffinate stream 504. The para-xylene depleted stream 504 is split into a purge stream 505 and an isomerization feed 506. Purge stream 505 can be used to control the concentration of

TABLE 2

| EB fraction in Feed to Loop (Stream 501) (%) | EB tolerance for separation (Stream 510) (%) | Raffinate Purge Fraction (%) | Feed Mass Rate (501) | Purge Mass Rate (506) | pX product Rate (503) |
|---|---|---|---|---|---|
| 1% | 10% | 2.0% | 1000 | 78 | 922 |
| 2% | 10% | 4.5% | 1000 | 160 | 840 |
| 5% | 10% | 15.9% | 1000 | 403 | 597 |
| 5% | 15% | 8.2% | 1000 | 271 | 729 |
| 5% | 20% | 5.3% | 1000 | 205 | 795 |
| 10% | 15% | 26.3% | 1000 | 546 | 454 |
| 10% | 20% | 14.4% | 1000 | 415 | 585 |
| 10% | 30% | 6.8% | 1000 | 282 | 718 |

Based on Table 2, reducing or minimizing the ethylbenzene content of the input feed to a xylene separation loop can have an unexpectedly large impact on the resulting yield. At ethylbenzene contents of 5 wt % or greater, even an extremely high tolerance for ethylbenzene of 20% results in only a separation purge ratio of greater than 0.25. By contrast, a feed with an ethylbenzene content of less than 5 wt % allows for substantially improved separation purge ratios of 0.2 or less, or 0.15 or less, or even 0.1 or less.

While the present invention has been described and illustrated with respect to certain aspects, it is to be understood that the invention is not limited to the particulars disclosed and extends to all equivalents within the scope of the claims. Unless otherwise stated, all percentages, parts, ratios, etc., are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed form any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

What is claimed is:

1. A method for forming para-xylene, comprising:
    a) separating a first $C_8$ aromatics stream and a $C_{9+}$ aromatics stream from an aromatic hydrocarbon feed stream having 5 wt % or less of aromatics with $C_{2+}$ side chains based on the total aromatics content of the aromatic hydrocarbon feed stream;
    b) exposing the $C_{9+}$ aromatics stream to effective transalkylation conditions in the presence of a continuous liquid phase and a transalkylation catalyst to form a transalkylation effluent having a greater weight percent of $C_8$ aromatics than the $C_{9+}$ aromatics stream, wherein the transalkylation catalyst comprises 0.1 wt % or less of a Group VIII metal and/or has an Alpha value of 10 or less;
    c) separating a second $C_8$ aromatics stream from the transalkylation effluent; and
    d) separating a para-xylene enriched fraction from the first $C_8$ aromatics stream and the second $C_8$ aromatics stream, the para-xylene enriched fraction having a greater weight percent of para-xylene than the weight percent of para-xylene in the first $C_8$ aromatics stream and the second $C_8$ aromatics stream.

2. The method of claim 1, further comprising converting a feed comprising methyl halide, methanol, dimethyl ether, or a combination thereof under effective aromatic formation conditions to produce an aromatic formation effluent, which comprises at least a portion of the aromatic hydrocarbon feed stream.

3. The method of claim 2, wherein the effective aromatic formation conditions comprise at least one of i) a conversion catalyst comprising a molecular sieve, the conversion catalyst being modified by addition of at least one element from Group 2 to Group 14; ii) a space velocity of 0.1 $hr^{-1}$ to 2.0 $hr^{-1}$; and iii) a temperature of 450° C. to 600° C.

4. The method of claim 2, wherein the effective aromatic formation conditions comprise introducing the feed comprising methyl halide, methanol, dimethyl ether, or a combination thereof into a reactor for performing the conversion using staged introduction of the feed.

5. The method of claim 2, wherein the aromatic formation effluent has a $C_9$ aromatics content of at least 45 wt % based on the total aromatics content of the aromatic formation effluent, a $C_{9+}$ aromatics content of at least 60 wt % based on the total aromatics content of the aromatic formation effluent, a $C_8$ aromatics content of 25 wt % or less based on the total aromatics content of the aromatic formation effluent, or a combination thereof.

6. The method of claim 2, wherein the aromatic formation effluent comprises aromatics with alkyl side chains, at least 90% of the alkyl side chains being methyl side chains.

7. The method of claim 1, wherein the aromatic hydrocarbon feed stream has a methyl-ethylbenzene content of 1 wt % or less based on the total aromatics content of the aromatic hydrocarbon feed stream, an isopropylbenzene content of 1 wt % or less based on the total aromatics content of the aromatic hydrocarbon feed stream, or a combination thereof.

8. The method of claim 1, wherein step d) further comprises separating a para-xylene depleted fraction from the first $C_8$ aromatics stream and the second $C_8$ aromatics stream, and further comprising:
    e) isomerizing the para-xylene depleted fraction to form an isomerized product stream having a greater weight percent of para-xylene than the weight percent of para-xylene in the para-xylene depleted fraction.

9. The method of claim 1, wherein step d) comprises a simulated moving bed separation process.

10. The method of claim 1, wherein the aromatic hydrocarbon feed stream is derived from an aromatic formation process comprising i) converting of methane to methanol, dimethyl ether, methyl bromide, methyl halide, or a combination thereof, and ii) converting the methanol, dimethyl ether, methyl bromide, methyl halide, or combination thereof under effective aromatic formation conditions to form an aromatic formation effluent, wherein the aromatic hydrocarbon feed stream comprises the aromatic formation effluent.

11. The method of claim 10, wherein the aromatic formation effluent comprises aromatics with alkyl side chains, at least 90% of the alkyl side chains being methyl side chains.

12. The method of claim 1, further comprising:
    f) separating a $C_6$-$C_7$ aromatics stream from the aromatic hydrocarbon feed stream; and
    g) supplying at least a portion of the $C_6$-$C_7$ aromatics stream to step b).

13. The method of claim 1, further comprising:
    h) separating a $C_6$-$C_7$ aromatics stream from the aromatic hydrocarbon feed stream;
    i) exposing at least a portion of the $C_6$-$C_7$ aromatics stream to effective methylation conditions to form a methylation effluent;
    j) separating a methylated $C_8$ aromatics stream from the methylation effluent; and
    k) separating a para-xylene enriched fraction from the methylated $C_8$ aromatics stream.

14. The method of claim 1, wherein the aromatic hydrocarbon feed stream has a $C_8$ aromatics content of 25 wt % or less based on the total aromatics content of the aromatic hydrocarbon feed stream.

* * * * *